United States Patent [19]
Fuhrberg et al.

[11] Patent Number: 5,849,007
[45] Date of Patent: Dec. 15, 1998

[54] HANDPIECE FOR THE DISTAL END OF A LIGHT GUIDE FOR LASER LIGHT

[75] Inventors: Gerald Fuhrberg, Hannover; Heinrich-Otto Teichmann, Göttingen, both of Germany

[73] Assignee: Fuhrberg Teichmann Windolph LISA laser products oHG, Germany

[21] Appl. No.: 755,324

[22] Filed: Nov. 21, 1996

[30] Foreign Application Priority Data

Nov. 21, 1995 [DE] Germany ......................... 295 18 434 U

[51] Int. Cl.⁶ .................................................. A61B 17/36
[52] U.S. Cl. .................................................. 606/13; 606/16
[58] Field of Search .................................. 606/15–16, 13, 606/7

[56] References Cited

U.S. PATENT DOCUMENTS

| | | | |
|---|---|---|---|
| 5,243,679 | 9/1993 | Sharrow et al. | 385/135 |
| 5,364,391 | 11/1994 | Konwitz | 606/16 |
| 5,409,483 | 4/1995 | Campbell et al. | 606/15 |

*Primary Examiner*—Jennifer Bahr
*Assistant Examiner*—Roy D. Gibson
*Attorney, Agent, or Firm*—Isaf, Vaughan & Kerr

[57] ABSTRACT

A handpiece for the distal end of a laser light guide includes a handle and a tube connected to the handle. The light guide enters the tube through the handle. The handpiece further includes opposed part of friction rolls for detachable fixing the light guide to the handle and a lever connected to one of the friction rolls for adjusting the position of the distal end of the light guide with respect to the distal end of the tube.

12 Claims, 2 Drawing Sheets

HANDPIECE FOR THE DISTAL END OF A LIGHT GUIDE FOR LASER LIGHT

FIELD OF THE INVENTIONS

The present invention relates to a handpiece for the distal end of a laser light guide. More particularly, the invention relates to a laser light guide handpiece comprising a handle and a tube connected to the handle whereby the light guide enters the tube through the handle; means for detachable fixing of the light guide to the handle; means for adjusting the position of the distal end of the light guide with respect to the distal end of the tube.

BACKGROUND OF THE INVENTION

Laser light guide handpieces serve for enabling the user to hold the distal end of a light a guide for a laser light which can be a covered with a mono fiber.

Handpieces that comprise a light guide which is located in and glued together with a guiding tube are known. The proximal end of the guiding tube made from special steel is formed as a handle. The disadvantage of this handpiece is the fact that while approaching the field of application with the distal end of the light guide (eg. during a medical operation) the end of the light guide extending from the guiding tube can be damaged. in addition the guiding tube is exposed to direct radiation by the laser after a certain amount of consumption of the light guide. With a powerful enough laser this can mean the destruction of the tube. The less the light guide extends from the tube for reasons of safety while approaching the field of application the bigger this danger grows.

Another known handpiece comprises a handle that covers the distal and of the light guides, whereby a guiding tube with a firmly glued-in section of the light guide can be connected to the handle When the guiding tube with the section of the light guiding can not be used any longer, this tube can be replaced without having to replace the whole light guide or the handle The disadvantage of this handpiece is the coupler point between the light guide and the section of the light guide inside the tube. At this coupler point high temperatures can derive from the absorption of laser radiation at small-sized dirt particles which can lead to the destruction of the handpiece.

With another known one-piece handpiece having a handle and a tube the firm connection of the handle with the tube results from a crimping operation. The disadvantage of this is the fact that the position of the distal end of the light guide cannot be changed with respect to the distal end of the tube after crimping. In addition also the handle cannot be used any longer after a damage done to the tube.

This disadvantage is eliminated by a handpiece in which the light guide is clamped at the proximal end of the handpiece. For adjusting the position of the light guide with respect to the tube a detachable threaded connection is provided. The disadvantage of this handpiece is the fact that the adjustment of the amount of extension of the light guide with respect to the tube has to be done with both hands, and in addition that this adjustment is combined with a turning of the tube with respect to the handle.

SUMMARY OF THE INVENTION

It in an object of this invention, therefore to provide a handpiece of the type mentioned above with an easy construction and especially easy operation.

According to the invention, this object is realized with the means for fixing and the means for adjusting having a common pair of friction rolls which are arranged perpendicularly to the main direction of extension of the light guide, between which the light guide can be clamped, and with which the light guide can me moved in its main direction of extension. The major components of the means for fixing and the means for adjusting are combined in the new handpiece. These major components consist of the two friction rolls which fix the light guide to the handle and in addition facilitate an adjustment of the position of the light guide with respect to the position of the tube. Therefore one of the friction rolls has to be turned in order to move the light guide located between the rolls back and forth. In order to provide a secure engagement by friction between the friction rolls and the normally covered light guide the friction rolls have a rough or profiled surface. This provides a secure translation during the process of turning the rolls on the one hand and a secure fixing while the rolls do not turn.

The preferred embodiment of this new handpiece comprises a spring which acts upon one of the friction rolls in the direction of the other friction roll with a clamping force for the light guide. The spring that can be possibly built by two flat spiral springs, presses the two parallel friction rolls against one another or clamps the light guide between the rolls, respectively. In this way the clamping force defined by the springs does not get too big for the light guide which makes damaging to the light guide by the friction rolls impossible. As a result the user does not have to care about whether the clamping force between the two friction rolls is big enough to hold the light guide or small enough to prevent the light guide from being damaged. Both goals are automatically achieved by the spring. This is even true while using light guides of different diameters if the spring is adjusted.

In order to adjust the position of the light guide with respect to the tube, a radially extending lever can be connected to one of the friction rolls. By swinging the lever the connected roll is turned. The engagement by friction with the light guide clamped between the two friction rolls causes the turning of the other roll.

Preferably the friction roll connected to the lever has a stationary bearing which also gives a stationary turning point to the lever.

The lever itself is preferably U-shaped, being connected to both ends of one of the rolls and covering the handle. In this manner the lever is easily accessible and unable.

The lever may not only be provided for adjusting the position of the light guide with respect to the tube but also for activating the means for fixing. For this reason the lever may comprise a guiding element, which in a certain angle position of the lever presses the two friction rolls away from one another against the clamping force of the spring. In this angle position the light guide is introduced into the handle and the tube in the beginning. As soon as the lever swings out of this position, the light guide is connected to the handpiece. A swinging hack of the lever results in another loosening of the light guide.

The guiding element can for example have a pin that extends axially and engages an axle stub of the biased friction roll. This pin lifts the axle stub and consequently the biased friction roll off the other friction roll while swinging the lever.

The lever may comprise a snap-in locking device with different angle positions in order not to lose an adjusted position of the light guide with respect to the tube.

Preferably the two friction rolls are located in the handle at the distal end thereof. At this point the means for adjusting and fixing can be easily manipulated by the user's thumb.

The tube does not serve for any fixing operation of the light guide in this new handpiece. In that way there are no limitations for the shape of the tube. Preferably the tube is connected detachably to the handle by means of a quick acting closure in order to enable an easy replacement in case of damage. An especially functional quick acting closure for the tube is known as a Luer-lock.

The invention is described and explained with respect to an embodiment.

DETAILED DESCRIPTION

Figure 1:
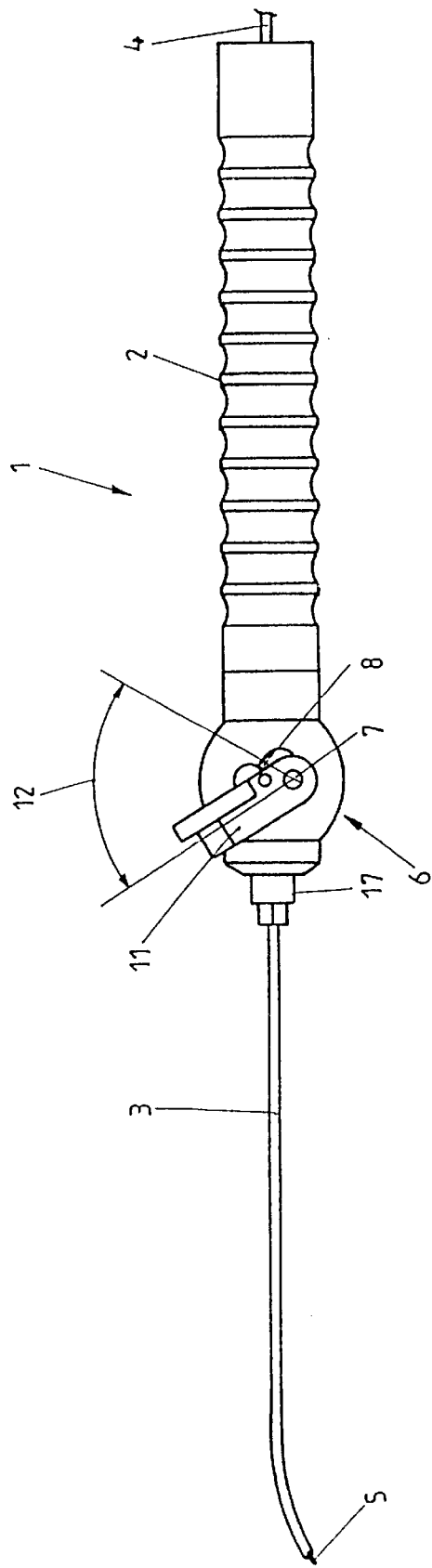
FIG. 1 is an elevational view of a preferred embodiment of the handpiece illustrating both, the tube and the handle.
Figure 2:
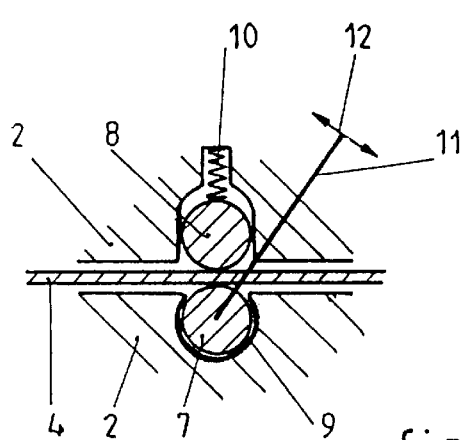
FIGS. 2–6 illustrate several details and positions of the components of the handpiece of FIG. 1.
Figure 3:
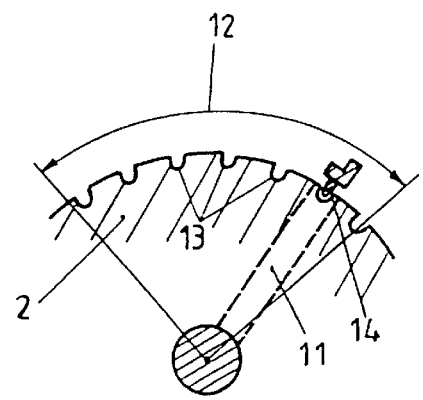

The handpiece 1 shown in FIG. 1 comprises a handle 2 and a tube 3. A light guide 4 for guiding the laser light extends through the handle 2 and the tube 3. The distal end 5 of the light guide 4 is located at the distal end of the tube and can emerge from the tube as shown. The tube 3 is replaceably connected with the handle 2 by a quick acting closure 17. This quick acting closure 17 is a Luer-lock as it is called. A mechanism for fixing and adjusting 6 the light guide 4, shown in greater detail in FIG. 2 to 6, are located at the distal end of the handle 2. A fundamental component of the mechanism for fixing and adjusting 6 is a pair of friction rolls 7 and 8. The friction roll 7 has a stationary bearing 9 at the handle 2. It is a simple sliding bearing which is formed by a bore in the handle 2. The friction roll a is biased by a spring 10 toward the parallel mounted friction roll 7. An this manner the light guide 4 located between the friction rolls 7 and 8 is clamped. A rough or profiled surface shape of the friction rolls 7 and 8 provides a secure engagement by friction between the light guide 4 and the friction rolls 7 and 8. In order to adjust the relative position of the light guide 4 a lever 11 is mounted on the stationary friction roll 7. By swinging the lever 11 in the direction of double arrow 12 the friction roll 7 is turned. Thereby the light guide 4 is moved back and forth. The friction roll 8 is turned by engagement by friction with the light guide 4. In FIG. 1 and 3 the double arrow 12 covers the whole range at adjustment of the lever 11. In this range of adjustment a snap-in locking device 13, 14 for the lever 11 in given angle positions is located. The snap-in locking device consists of a pit 13 in the handle 2 which engages with the flexible locking nose 14 in the given angle positions. The lever 11 can be turned easily by the user's thumb in order to adjust the relative position of the light guide 4 and especially the position of the distal end 5 of the light guide 4 relative to the distal end of the tube 3. It is the thumb of the hand holding the handle 2 which facilitates an easy one-handed operating of the means for fixing and adjusting 6.

Figure 4:
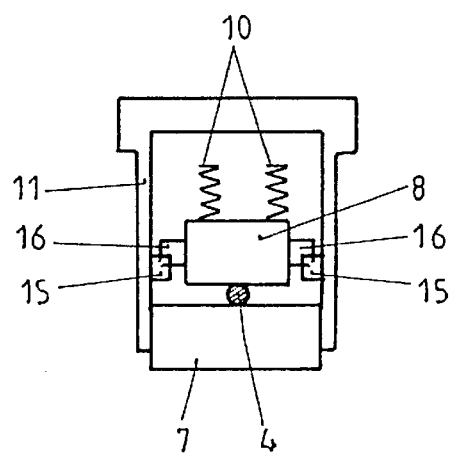
Figure 6:
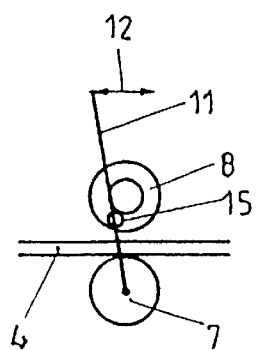
Figure 5:
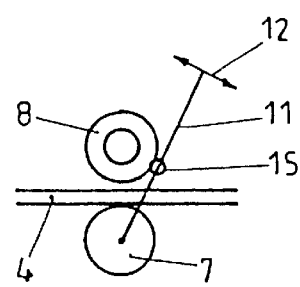

FIGS. 4 to 6 show how this one-handed operation also includes the fixing function. FIG. 4 shows the arrangement of the lever 11 and the two friction rolls 7 and 8 in which the viewing direction is in alignment with the main direction of extension of the light guide 4. It can be seen in FIG. 4 that the lever 11 is designed in a U-shape and contacts the friction roll 7 with both ends. Thereby it encompasses the handle 2 not shown in FIG. 4. Two pins 15 extend radially inwardly from the lever 11. By swinging the lever 11 about the bearing axis of the friction roll 7, the pins 15 meet axle stubs 16 of the friction roll 8 biased by a spring. During subsequent swinging of the lever 11 the pins 15 lift the axle stubs 16 and thereby the friction roll 8. As a result the light guide 4 is not clamped any longer. This is illustrated in FIG. 6. It can be also seen in FIG. 6 that the pins 15 extend a little through the surface plane built by the axes of the friction rolls 7 and. 8 which facilitates an automatic securing of the position of the lever 11. In this position the light guide 4 can be introduced into the handle 2 and the tube 3. Afterwards the light guide 4 is clamped between the friction rolls by swinging back the lever 11 and thereby lowering the friction roll 8 towards the friction roll 7. The new handpiece only comprises the lever 11 as an operating element. Nevertheless a complex and easy manipulation of the light guide is possible with this operating element.

LIST OF REFERENCE NUMERALS 1 handpiece
2 handle
3 tube
4 light guide
5 distal end
6 mechanism for fixing and adjusting
7 friction roll
8 friction roll
9 bearing
10 spring
11 lever
12 double arrow
13 pit
14 locking nose
15 pin
16 axle stub
17 quick acting closure

We claim:

1. A handpiece for receiving and holding the distal end of an elongate laser light guide, the handpiece comprising:
   a handle;
   an elongate tube connected to the handle, said tube having a distal end and being sized and shaped so that the light guide may be passed into the tube through said handle;
   means for detachably fixing the light guide to said handle; and
   means for adjusting the position of the distal end of the light guide with respect to the distal end of the tube;
   wherein said means for adjusting and said means for fixing comprise a common pair of friction rolls positioned perpendicularly with respect to the length of the light guide and between which the light guide is clamped, said friction rolls being constructed and arranged to permit movement of the light guide along its length therebetween, and a rotation apparatus operatively connected to one of said friction rolls, said rotation apparatus, when moved, imparting rotation to said one of said rolls to adjust the position of the distal end of the light guide.

2. The handpiece of claim 1, wherein said friction rolls are biased toward one another by a spring, said sprint being sized and shaped to bias one of said friction rolls toward the other of said friction rolls with a clamping force for engaging the light guide therebetween.

3. The handpiece of claim 2, wherein a radially extending lever is connected to at least one of said friction rolls.

4. The handpiece of claim 1, wherein said rotation apparatus comprises a radially extending lever connected to said one of said friction rolls.

5. The handpiece of claim 4, wherein said one of said friction rolls connected to the lever has a stationary bearing.

6. The handpiece of claim 4, wherein said lever is U-shaped and is connected to both of the ends of said one of said friction rolls, said lever being sized and shaped to surround the handle.

7. The handpiece of claim 4, wherein said lever includes a snap-in locking device constructed and arranged to lock said lever in one of a plurality of different angle positions with respect to said one of said friction rollers.

8. The handpiece of claim 1, further comprising a quick acting closure constructed and arranged to detachably connect said tube to said handle.

9. A handpiece for receiving and holding an elongate laser light guide, the laser light guide having a proximal end and a distal end, said handpiece comprising:

an elongate handle;

an elongate tube connected to said handle, said tube having a proximal end and a distal end, said tube being sized and shaped for passage of the distal end of the light guide through said distal end of said tube;

means for detachably affixing the light guide to said handle; and means for adjusting the position of the distal end of the light guide with respect to said distal end of said tube;

said means for adjusting the distal end of the light guide, and said means for detachably affixing the light guide comprising a common pair of friction rolls supported on said handle and positioned perpendicularly with respect to the length of the light guide and between which the light guide is clamped, said friction rolls being constructed and arranged for movement of the light guide along its length therebetween, and a rotation apparatus operatively connected to at least one of said friction rolls, said rotation apparatus, when moved, imparting rotation to said at least one of said rolls to adjust the position of the distal end of the light guide.

10. The handpiece of claim 3, wherein said lever has a guiding element constructed and arranged to press said lever in a predetermined angled position thereof against the clamping force of said spring to move said friction rolls away from each other.

11. The handpiece of claim 10, wherein said guiding element comprises an axially extending pin, said pin being constructed and arranged to engage an axle stub of a spring-biased friction roll.

12. (New) A handpiece for receiving and holding the distal end of an elongate laser light guide, said handpiece comprising:

a handle;

an elongate tube connected to said handle, said tube having a distal end and being sized and shaped so that the light guide may be passed into said tube through said handle;

means for detachably fixing the light guide to said handle; and means for adjusting the position of the distal end of the light guide with respect to said distal end of said tube by imparting movement to the light guide;

wherein said means for adjusting and said means for fixing comprise a pair of friction rolls positioned perpendicularly with respect to the length of the light guide and between which the light guide is clamped, said friction rolls being constructed and arranged to permit movement of the light guide along its length therebetween.

\* \* \* \* \*